United States Patent [19]

Teodorescu et al.

[11] Patent Number: 6,011,477
[45] Date of Patent: Jan. 4, 2000

[54] RESPIRATION AND MOVEMENT MONITORING SYSTEM

[75] Inventors: Horia-Nicolai Teodorescu, Iasi, Romania; Daniel J. Mlynek, Preverenges, Switzerland

[73] Assignee: Sensitive Technologies, LLC, Portland, Oreg.

[21] Appl. No.: 09/120,042

[22] Filed: Jul. 21, 1998

Related U.S. Application Data

[63] Continuation-in-part of application No. 09/004,108, Jan. 7, 1998, Pat. No. 5,986,549.
[60] Provisional application No. 60/059,450, Sep. 22, 1997, and provisional application No. 60/053,543, Jul. 23, 1997.

[51] Int. Cl.⁷ ................................................. G08B 23/00
[52] U.S. Cl. ........................................ 340/573.1; 340/575
[58] Field of Search ........................... 340/573.1, 573.7, 340/575, 572.5

[56] References Cited

U.S. PATENT DOCUMENTS

| | | | |
|---|---|---|---|
| 3,371,272 | 2/1968 | Stanton | 324/34 |
| 3,796,208 | 3/1974 | Bloice | 128/721 |
| 3,911,899 | 10/1975 | Hattes | 118/2 S |
| 4,267,522 | 5/1981 | Periot | 331/65 |
| 4,279,257 | 7/1981 | Hochstein | 128/722 |
| 4,328,433 | 5/1982 | Nodera et al. | 307/311 |
| 4,433,693 | 2/1984 | Hochstein | 128/721 |
| 4,438,771 | 3/1984 | Friesen et al. | 128/671 |
| 4,474,185 | 10/1984 | Diamond | 128/671 |
| 4,502,042 | 2/1985 | Wührl et al. | 340/568 |
| 4,679,036 | 7/1987 | Cheng | 340/573.1 |

(List continued on next page.)

FOREIGN PATENT DOCUMENTS

| | | | |
|---|---|---|---|
| 0205931 | 12/1986 | European Pat. Off. | A61B 5/10 |
| 80541 | 7/1981 | Romania | G01B 7/14 |
| 94279 | 1/1986 | Romania | G08B 13/26 |
| 9500904 | 5/1995 | Romania | G01C 21/00 |
| 112918B | 1/1998 | Romania | G01D 5/243 |
| 9636279 | 11/1996 | WIPO | A61B 5/113 |

OTHER PUBLICATIONS

"KinderTec launches baby monitor", Paul Durman, The Times, London, UK, May 25, 1998.
"Methods to Assess Physical Activity . . . Reference to Motion Sensors and Accelerometers", Meijer et al., IEEE Transactions on Biomedical Engineering, vol. 38, No. 3, Mar. 1991, pp. 221–229.

*Primary Examiner*—Jeffery A. Hofsass
*Assistant Examiner*—Toan Pham
*Attorney, Agent, or Firm*—Stoel Rives LLP

[57] ABSTRACT

A monitoring system (10) of this invention includes a first sensor (12) for detecting the respiration and/or movements of an infant (14), and an optional second sensor (18) for detecting the presence and/or movement of the infant or proximal objects (20) surrounding the infant. An optional accelerometric sensor (22) detects movements of a platform (16) supporting the infant and contributes supplementary movement data to the monitoring system. An optional audio sensor (24) detects sounds associated with the infant or proximal objects. None of the sensors are physically attached to the infant. A controller (26) conditions and processes the various sensor signals and generates alarms by interpreting the sensor signals. The controller optionally communicates with a remote control unit (30). In one embodiment, the first sensor signal is filtered (112, 114) to extract respiration- and nonrespiration-related signals that are processed by a signal processor (116), which compares the extracted signals to thresholds, and if neither signal exceeds its threshold for a predetermined time, a low signal alarm is generated. In another embodiment, the signal processor determines whether a respiration decay period is less than a threshold value, and if not, generates a respiration decay alarm. In yet another embodiment, the signal processor compares the respiration-related signal pattern to a stored pattern, and if the patterns do not match, a respiration pattern alarm is generated. The signal processor further interprets various combinations of the sensor signals and makes aggregated decisions to generate specific warnings when critical situations occur.

31 Claims, 3 Drawing Sheets

U.S. PATENT DOCUMENTS

| | | | |
|---|---|---|---|
| 4,738,264 | 4/1988 | Orlando | 128/671 |
| 4,851,816 | 7/1989 | Macias et al. | 340/573.1 |
| 4,853,692 | 8/1989 | Wolk et al. | 340/573 |
| 4,895,160 | 1/1990 | Reents | 128/671 |
| 4,958,638 | 9/1990 | Sharpe et al. | 128/653 R |
| 5,081,722 | 1/1992 | Yu | 5/99.1 |
| 5,184,112 | 2/1993 | Gusakov | 340/573.1 |
| 5,241,300 | 8/1993 | Buschmann | 340/573.1 |
| 5,291,013 | 3/1994 | Nafarrate et al. | 250/227.14 |
| 5,309,921 | 5/1994 | Kisner et al. | 128/719 |
| 5,347,669 | 9/1994 | Neviaser et al. | 5/655 |
| 5,410,297 | 4/1995 | Joseph et al. | 340/573.7 |
| 5,446,934 | 9/1995 | Frazier | 5/655 |
| 5,479,932 | 1/1996 | Higgins et al. | 128/671 |
| 5,505,199 | 4/1996 | Kim | 128/633 |
| 5,515,865 | 5/1996 | Scanlon | 128/721 |
| 5,611,349 | 3/1997 | Halleck et al. | 128/721 |
| 5,862,803 | 1/1999 | Besson et al. | 660/508 |

RESPIRATION AND MOVEMENT MONITORING SYSTEM

RELATED APPLICATIONS

This application claims priority from U.S. Provisional application Ser. No. 60/059,450, filed Sep. 22, 1997, for RESPIRATION AND MOVEMENT MONITORING SYSTEM and is a continuation-in-part of U.S. patent application Ser. No. 09/004,108, filed Jan. 7, 1998, for POSITION AND MOVEMENT RESONANT SENSOR, now U.S. Pat. No. 5,986,549, which claims priority from U.S. Provisional application Ser. No. 60/053,543, filed Jul. 23, 1997 for POSITION AND MOVEMENT RESONANT SENSOR.

TECHNICAL FIELD

This invention relates to a biomedical respiration and movement monitoring system and more particularly to an apnea, sleep monitoring (polysomnography), and sudden infant death syndrome (SIDS) monitoring system that further monitors and interprets the presence and movements of objects in the vicinity of a subject being monitored.

BACKGROUND OF THE INVENTION

There are previously known systems for monitoring either respiratory signals, or movements of a subject during sleep and especially for detecting SIDS-related apnea or respiratory cessation in infants aged 0 to 24 months. Such systems typically employ movement and force transducers, such as accelerometers, and respiration (pneumographic) flow, volume, or thorax movement transducers. An exemplary prior system is the BABYSENSE monitoring system manufactured by Hi Sense, Ltd., located in Shilat, Israel.

Sleep analysis software products are also available for analyzing in a computer, data received from sensors, such as the above-described transducers. An exemplary software product is the SLEEP ANALYSIS SYSTEM FOR WINDOWS, manufactured by Datasystmeter A/S, located in Aalborg, Denmark.

Unfortunately, such transducers, systems, and software products typically have one or more disadvantages including unreliable respiration and respiration cessation detection, inability to distinguish between respiratory movements and other movements, unsuitability for home usage (commercial configurations), unsuitability for infant monitoring (adult scale factors), and a relatively high expense (require a computer, software, and interconnecting cables). Moreover, most require a physical attachment to the monitored, which attachment limits natural movements and creates psychological side effects.

What is needed, therefore, is a low cost, sensitive, and reliable respiration and movement monitoring system that does not require any physical attachments to the monitored and that is suitable and safe for home, commercial, or institutional use on infants and adults alike.

SUMMARY OF THE INVENTION

An object of this invention is, therefore, to provide an apparatus and a method for monitoring the respiration and/or movements of a subject, such as an infant, without requiring a physical attachment to the monitored subject.

Another object of this invention is to provide an apparatus and a method for safely and effectively monitoring the respiration and/or movements of an infant human subject.

A further object of this invention is to provide an apparatus and a method for monitoring various biomedical parameters of an infant and generating associated low error rate alarm signals based on interpreting the parameters in light of the infant's age.

A monitoring system of this invention includes a first sensor for detecting the respiration and/or movements of an infant, and an optional second sensor for detecting the presence and/or movement of the infant or proximal objects relative to a predetermined "safety perimeter" surrounding the infant. An optional accelerometric sensor detects movements of a platform supporting the infant and contributes supplementary movement data to the monitoring system. An optional audio detector detects sounds associated with the infant or proximal objects. A controller conditions and processes the signals received from the various sensors and generates or inhibits alarms consistent with the signals detected. The controller optionally communicates with a remote control unit.

In one embodiment the first sensor signal is filtered to extract respiration- and nonrespiration-related signals that are processed by a signal processor, which compares the signal values of the extracted signals to predetermined thresholds, and if neither signal exceeds its threshold for a predetermined time period, a low signal alarm is generated.

In another embodiment, the signal processor generates from the respiration-related signal a self-correlation signal and determines the decay period of the correlation signal. If the decay period is less than a predetermined threshold value, a respiration decay alarm signal is generated.

In yet another embodiment, the processing system first performs a feature extraction process, then a classification and pattern recognition process, and finally a decision making processes. In all these processes, the system may employ some combination of binary or fuzzy logic-based techniques. Moreover, for the classification process, the system may include or simulate nonlinear signal processors or classifiers, such as neural networks. The decision-making process includes generating an alarm signal or a class of pre-alarm (warning) and alarm signals.

In still another embodiment, the signal processor performs a pattern matching operation in which a period of the respiration-related signals is processed to store a respiration-related period pattern in a memory. The signal processor compares a subsequently received respiration-related signal period to the previously stored period pattern. If a pattern matching does not occur, a respiration pattern alarm is generated.

In further embodiments, if the monitoring system includes the optional second sensor and the second sensor signal does not exceed a predetermined threshold, then the infant is interpreted as laying down. If the second sensor signal exceeds the predetermined threshold, an abnormality alarm is generated. If the second sensor signal does not exceed the predetermined threshold and is not correlated with movements detected by the first sensor signal, then the situation is interpreted as an external object approaching the second sensor, and a safety perimeter intrusion alarm is generated. If the monitoring system includes the optional audio detector and a sensed audio signal exceeds a predetermined threshold, the situation is interpreted as a vocal sound from the infant and alarms are inhibited. If the monitoring system includes the humidity sensor and a detected moisture level exceeds a predetermined threshold, the situation is interpreted as incontinence of the infant, and an incontinence alarm is generated.

In still further embodiments, the system may includes additional sensors for generating biological signals from the infant, such as electrocardiograph ("ECG") and blood oxygen saturation signals that are analyzed together with the respiratory and movement signals to render a decision on the state of the infant and generate appropriate warnings or alarms. The system may also include a sleeping position sensor to generate warnings when the infant is in an incorrect position, such as a prone position. Moreover, the system may include ambient condition sensors for monitoring SIDS risk factors, such as the sleeping environment temperature.

The signal processor further interprets the above-described alarm and alarm inhibitor signals and makes aggregated decisions to generate specific warnings when a critical situation occurs, such as when no respiration-related signal is detected during a predetermined time period, when an intruder enters the safety perimeter surrounding the infant, or when an abnormality is detected.

Additional objects and advantages of this invention will be apparent from the following detailed description of preferred embodiments thereof that proceed with reference to the accompanying drawings.

DETAILED DESCRIPTION OF PREFERRED EMBODIMENTS

Figure 1:
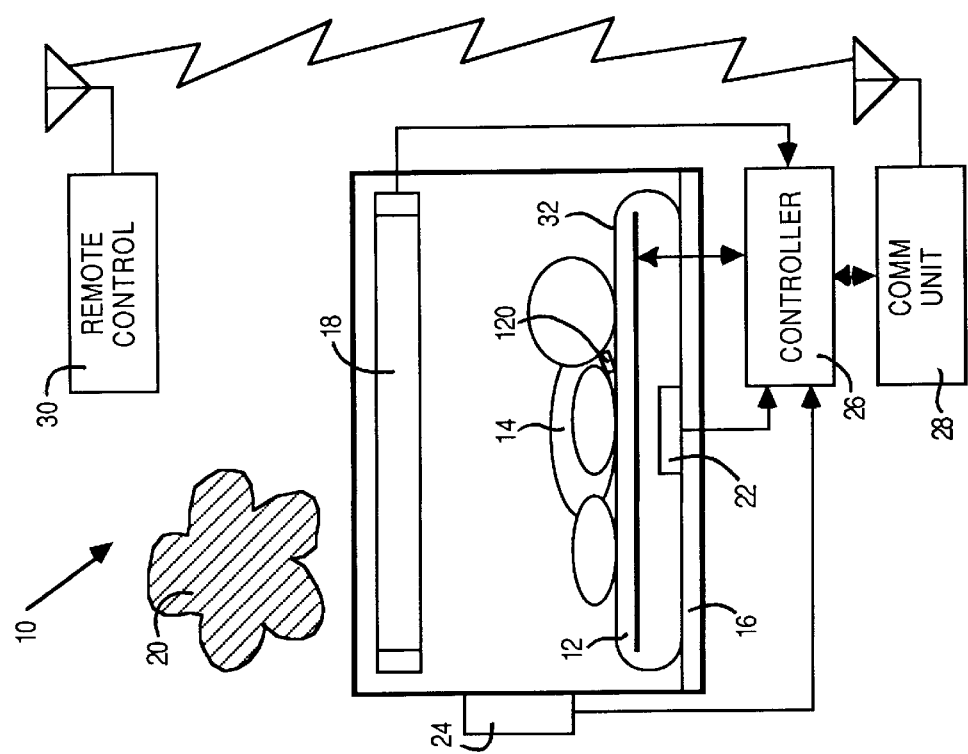
FIG. 1 is a simplified pictorial and electrical block diagram of a respiration and movement monitoring system of this invention.

FIG. 1 shows a respiration and movement monitoring system ("monitoring system") 10 of this invention includes a first sensor 12 for detecting the respiration and/or movements of a infant 14, or other suitable subject on a support platform 16, such as a bed, crib, or incubator. At least one optional, second sensor 18 detects the presence and/or movement of an external proximal object 20, such as a person or an animal. Moreover second sensor 18 detects movements of support platform 16 caused by vibrations and also detects movements of infant 14, such as when standing. Second sensor 18 is preferably placed around a predetermined "safety perimeter" surrounding infant 14 and, therefore, acts as a safety perimeter sensor.

At least one optional accelerometric sensor 22 detects movements of support platform 16. Accelerometric sensor 22 contributes supplementary movement data to monitoring system 10, and thus improves the interpretation of movement and respiration signals. Accelerometric sensor 22 may include any combination of piezoelectric, magnetostrictive, integrated circuit, and electromechanical sensor technology.

An optional audio detector unit 24 detects, filters, and amplifies audio signals produced proximal to support platform 16 by, for example, a voice or sounds associated with infant 14 or external proximal object 20.

A controller 26 includes signal conditioning and signal processing circuitry for processing data received from first sensor 12, second sensor 18, accelerometric sensor 22, and audio detector unit 24 and to generate or inhibit alarm conditions consistent with the signals detected. Controller 26 may optionally include a communication unit 28 for transmitting control and alarm condition data between monitoring system 10 and an optional remote control unit 30.

First sensor 12 is preferably enclosed within a textile fabric or flexible plastic material cover 32, such as a comforter, quilt, sheet, bedspread, fancy, or otherwise suitable enclosure that is placed on top of support platform 16. First and second sensors 12 and 18 have a sensing area that encompasses substantially all of the region proximal to monitoring system 10 with the possible exception of remote control unit 30.

First and second sensors 12 and 18 are embodiments of a resonant sensor that is described in more detail below with reference to FIGS. 2–7 and in U.S. patent application Ser. No. 09/004,108, filed Jan. 7, 1998, for POSITION AND MOVEMENT RESONANT SENSOR.

Figure 2:
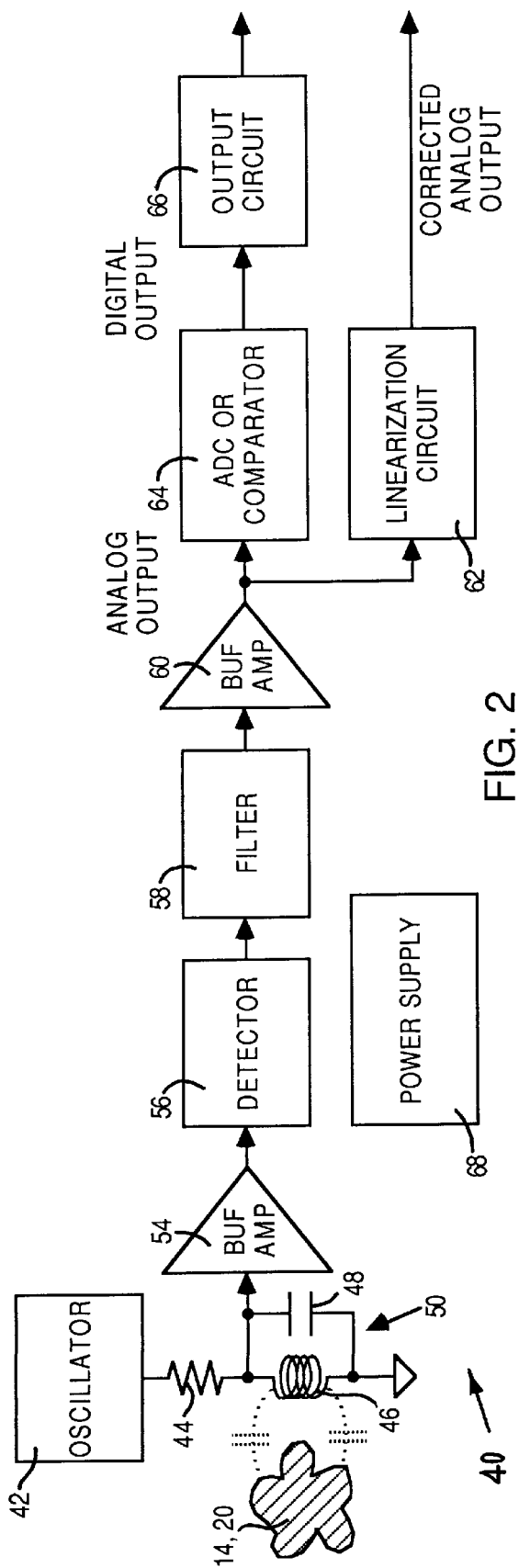
FIG. 2 is a simplified overall electrical block diagram of a sensor subsystem used in the respiration and movement monitoring system of FIG. 1.

FIG. 2 shows a sensor subsystem 40 suitable for implementing first and second sensors 12 and 18 and most of controller 26. Sensor subsystem 40 includes an oscillator 42 that couples through a relatively high-impedance 44 to a sensing element 46 a signal having a predetermined frequency. Sensing element 46 is preferably an inductor that is electrically connected in parallel with its equivalent capacitance or a capacitor 48 to form a parallel resonant sensor 50 that is tuned to, or close to, the predetermined frequency of oscillator 42. High-impedance 44 and resonant sensor 50 form a voltage divider circuit that generates at their junction a signal that is directly representative of a position and/or movement of, for example, infant 14 or external proximal object 20 in proximity to resonant sensor 50. In general, the proximity of infant 14 to resonant sensor 50 causes a change in the parallel resonant frequency of resonant sensor 50, which causes corresponding changes in its impedance and, therefore, the magnitude of the signal across resonant sensor 50. Skilled workers will recognize that the term resonant sensor 50 may be used interchangeably with first sensor 12 and second sensor 18.

Oscillator 42 preferably couples across resonant sensor 50 a radio-frequency ("RF") signal that generates within the sensing area an electromagnetic field having a field strength within the same order of magnitude as the field strength created by commercial radio and television broadcasting stations, thereby operating within Federal Communications Commission field emission and susceptibility rules.

To minimize loading of the signal across resonant sensor 50, a high input impedance buffer amplifier 54 having a low input capacitance conveys the signal to a detector 56 that extracts a peak or average envelope voltage value from the signal. Skilled workers will understand how to trim the parallel resonant frequency of resonant sensor 50 to account for the input capacitance of buffer amplifier 54. The peak envelope voltage is conditioned by a filter 58 and an amplifier 60 to produce an analog output signal.

An optional linearization circuit 62 receives the conditioned signal from amplifier 60 and applies a square-law, log, or piecewise linear conversion, as appropriate, to produce a corrected analog output signal. The correction is typically added to linearize the output voltage as a function of a distance between resonant sensor 50 and infant 14 or external proximal object 20.

In a digital measurement application, an analog-to-digital converter ("ADC") 64 receives and digitizes the conditioned analog signal from amplifier 60 and conveys it to a digital output circuitry 66 to produce a processed digital output signal. The processing may employ digital filtering, square-law, log, or lookup table conversions, as appropriate, to produce a processed digital output signal.

Sensor subsystem 40 is powered by a conventional power supply 68.

As mentioned above, digital output circuitry 66 may further include signal processing circuits. When infant 14 undergoes respiration and other movements, resonant sensor 50 detects the movement, and the corresponding signal is conditioned through sensor subsystem 40 as generally described above. Then output circuitry 66 further processes the signal to extract desired movement frequencies, such as respiration-related frequencies, and to detect and generate predetermined alarm conditions. Preferably, band-pass filtering is used to extract the respiration-related signal, and stop-band filtering is used to extract non-respiration related signals. The filtering and extraction functions can be implemented in hardware, software, or a combination of both. Preferably, the filter frequencies are tunable to adapt to the average age-related respiration rate of the particular infant or subject being monitored. In general, when sensing movements, the resonant frequency of resonant sensor 50 should be much higher (i.e., 10 times higher) than the highest object movement frequency expected. Signal processing is described in more detail with reference to FIG. 8.

Figure 3:
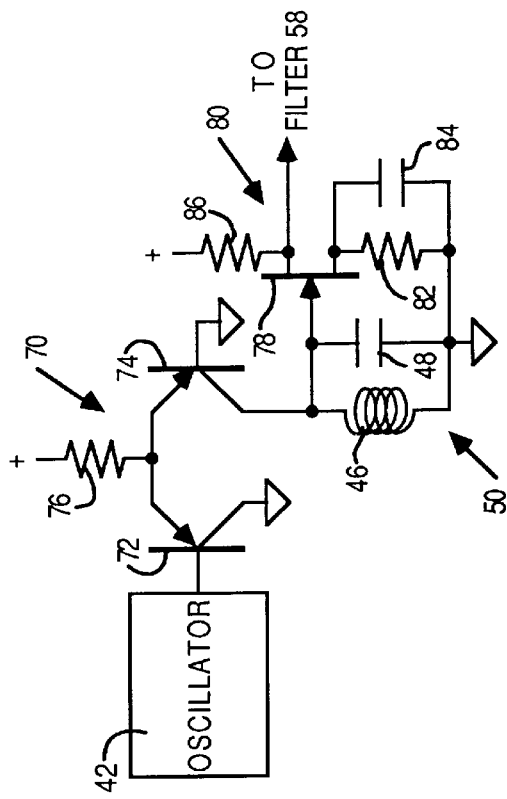
FIG. 3 is a simplified electrical schematic diagram showing alternative oscillator to sensor coupling and detector circuits of the sensor subsystem of FIG. 2.

FIG. 3 shows alternative embodiments of high impedance 44, buffer amplifier 54, and detector 56. As a general rule, the sensitivity of sensor subsystem 40 is directly proportional to the quality factor ("Q") of resonant sensor 50. A preferred embodiment of resonant sensor 50 is described below with reference to FIG. 4. Because Q is adversely affected by losses, resonant sensor 50 is preferably manufactured with low-loss electric and magnetic materials and loaded as lightly as practical to maintain a Q ranging from about 30 to about 100 at the operating frequency.

Major sources of loading include high-impedance 44, buffer amplifier 54, and coupling to infant 14 or external proximal object 20. High-impedance 44 is preferably a high-value resistor that lightly couples oscillator 42 to resonant sensor 50. The light coupling also reduces "pulling" of the predetermined frequency of oscillator 42 and reduces to an acceptable level RF energy radiating from resonant sensor 50.

An alternative embodiment of high-impedance 44 is a voltage-to-current converter 70 formed by a pair of transistors 72 and 74 connected in a differential current-steering configuration in which the emitters of transistors 72 and 74 are electrically connected together and to one end of a bias current determining resistor 76. The other end of resistor 76 is connected to a fixed voltage source. Oscillator 42 is electrically connected to the base of transistor 72. The base of transistor 74 is preferably grounded. The collector of transistor 74 provides to resonant sensor 50 a high-impedance alternating current version of the voltage waveform generated by oscillator 42.

Other alternatives for reducing the loading of resonant sensor 50 by oscillator 42 include connecting high-impedance 44 to a low-impedance tap (not shown) on sensing element 46 or to a low-impedance tap (not shown) on capacitor 48, when it exists as a discrete component. Such a tapped capacitor is readily formed by electrically connecting in series a pair of capacitors having the same equivalent value as capacitor 48. The junction between the two capacitors forms the tap. A low-impedance tap is implemented by choosing one capacitance value much larger than the other and connecting one end of the larger value capacitor to ground.

An alternative embodiment of buffer amplifier 54 and detector 56 may be implemented by employing a high-input impedance field-effect transistor ("FET") 78 as a combined buffer amplifier and peak detector 80. The gate-to-source junction of FET 78 forms a diode peak detector, the detected voltage of which forms across a source resistor 82 and is stored by a capacitor 84. A buffered, and amplified if desired, version of the source voltage is developed across a drain resistor 86 connected to the drain of FET 78. Skilled workers will understand how to further combine elements of filter 58 into combined buffer amplifier and peak detector 80. Likewise, the coupling of combined buffer amplifier and peak detector 80 to resonant sensor 50 may also employ a tap as described above. Indeed, the same tap or different taps may be employed by oscillator 42 and buffer amplifier 54 or their alternative embodiments.

Figure 4:
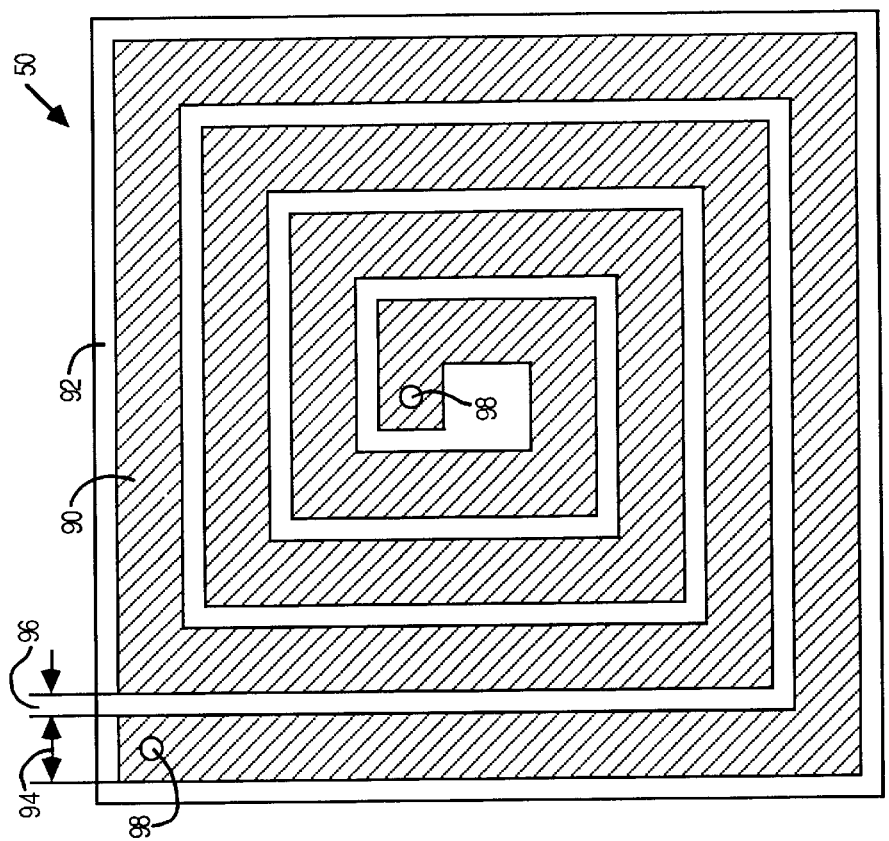
FIG. 4 is a pictorial plan view of a first preferred embodiment of a resonant sensor used in the subsystem of FIG. 2 showing the resonant sensor in a substantially planar spiral configuration.

FIG. 4 shows a preferred embodiment of resonant sensor 50 including a planar spiral winding 90 formed as a flexible printed circuit element, but which may be bonded to, pasted on, imprinted in, deposited over, etched on, or otherwise applied to a dielectric substrate 92. Winding 90 is preferably formed from a conductive polymeric material having a flexibility and a mechanical fracture resistance that improves the mechanical reliability of resonant sensor 50. Likewise, dielectric substrate 92 is preferably a substantially planar, flexible plastic material that conforms to a shape of a supporting form to which it is bonded, glued, housed, or otherwise attached. Moreover, dielectric substrate 92 preferably has a low relative dielectric constant "$\epsilon$" ranging from about 1.0 to about 5.0 to improve the sensitivity of resonant sensor 50 to proximal dielectric objects.

Planar winding 90 has a relatively large conductor width 94 and a relatively small spacing 96 between successive turns to achieve a suitably high capacitance between the turns and a suitably large overall capacitance for resonant sensor 50. The ratio of spacing 96 to conductor width 94 should be kept low (1:1 or less) to maximize the distributed capacitance of resonant sensor 50. The winding is shaped to provide a relatively uniform electric field in an object sensing zone that is generally determined by the overall dimensions and shape of resonant sensor 50. Such an electrical field is suitable for sensing dielectric (nonconductive and nonmagnetic) objects, such as infant 14.

A suitable effective capacitance for resonant sensor 50 is achieved by forming planar winding 90 in a strip-like shape in which conductor width 94 optimizes the conductive surface area of resonant sensor 50. A large distributed capacitance is particularly useful for sensing magnetic objects that also have a high electrical conductivity, which objects are best sensed at frequencies below 1 MHz.

Resonant sensor 50 may alternatively be implemented with conventional wires or by thin- or thick-film deposition of planar winding 90. Moreover, resonant sensor 50 is not limited to a particular size or shape and may, for example, have an overall square, rectangular, elliptical, or circular shape and a size (planar area) ranging from about 1 square millimeter to about 10 square meters. For relatively small sensors, e.g., less than about 1 square centimeter, an external capacitance may be connected in parallel with terminals 98 of resonant sensor 50 to reduce its resonant frequency. However, this also decreases the sensitivity of the sensor, mainly to dielectric objects. Of course, an external capacitor may be connected in parallel with any size of resonant sensor 50 to tune it to a predetermined frequency. For the above-described shapes and sizes of resonant sensor 50, oscillator 42 operating frequency is typically in a range from about 1 MHz to about 30 MHz.

In contrast to conventional inductor/capacitor ("LC") circuits that intentionally minimize "undesirable parasitic" capacitances and couplings to surrounding objects, resonant sensor 50 of this invention enhances the parasitic capacitances and couplings and employs them as sensitive object-sensing elements.

Figure 5:
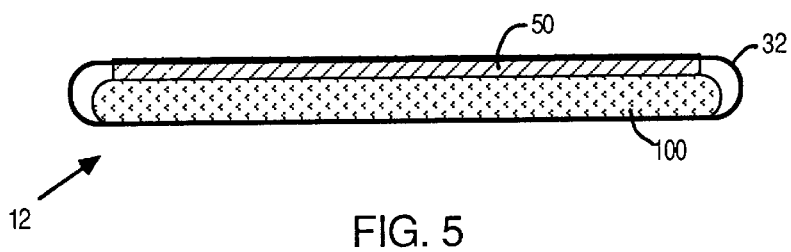
FIG. 5 is a sectional elevation view of a first preferred embodiment of the resonant sensor of FIG. 4 showing it enclosed in a cover and positioned adjacent to a sponge sheet.

FIG. 5 shows a first embodiment of first sensor 12 in which resonant sensor 50 is formed as a large, flexible, planar element positioned adjacent to a similarly large, flexible, planar first sponge sheet 100 that allows for a sensitivity-increasing deformation of resonant sensor 50 caused by movements of infant 14. Resonant sensor 50 and first sponge sheet 100 are enclosed in and protected by cover 32. The dimensions of first sponge sheet 100 are about the same as the dimensions of support platform 16 (FIG. 1) or slightly smaller, for example, about 5 centimeters less than support platform 16 on all margins.

Figure 6:
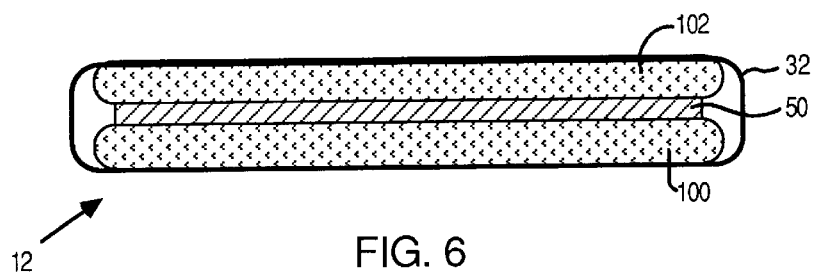
FIG. 6 is a sectional elevation view of a second preferred embodiment of the resonant sensor of FIG. 4 showing it enclosed in a cover and positioned between a pair of sponge sheets.

FIG. 6 shows a second embodiment of first sensor 12 in which resonant sensor 50 is again formed as a large, flexible, planar element, which in this embodiment is positioned between first sponge sheet 100 and a similar second sponge sheet 102. This embodiment provides not only the sensitivity-increasing deformation of resonant sensor 50 but also protects it from sharp movements or localized high pressures, such as can be caused when infant 14 stands up. As before, resonant sensor 50 and first and second sponge sheets 100 and 102 are enclosed in and protected by cover 32, and the overall areas of first and second sponge sheets 100 and 102 are about the same as the area of support platform 16 with the overall area of resonant sensor 50 being about the same or slightly smaller.

Figure 7:
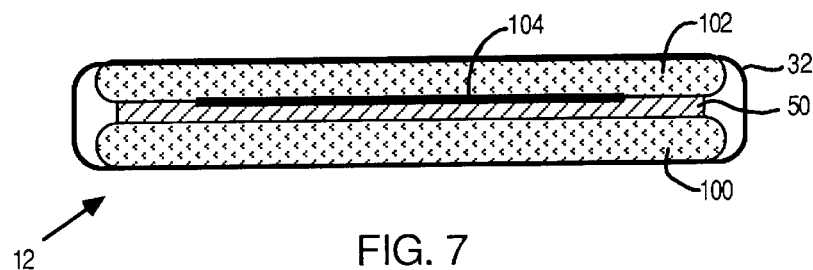
FIG. 7 is a sectional elevation view of an alternative embodiment of the resonant sensor of FIG. 6 showing it enclosed in a cover, positioned between a pair of sponge sheets, and further including a humidity sensor.

FIG. 7 shows an alternative embodiment of first sensor 12 further including a humidity sensor 104 that is positioned adjacent to resonant sensor 50. Humidity sensor 104 serves to determine incontinence of infant 14 and acts to further increase or decrease the sensitivity of first sensor 12 to certain movements of infant 14. The area, positioning, and degree of flexibility of humidity sensor 104 coact to determine which movements of infant 14 are increased or decreased in sensitivity. Preferably, humidity sensor 104 has about the same dimensions and rigidity as first sensor 12.

Referring to FIGS. 1, 5, 6, and 7, in any of the above-described embodiments, first sensor 12 detects the movements of infant 14, such as a child resting on first sensor 12, with cover 32 implemented as a comforter enclosing resonant sensor 50 and first and second sponge sheets 100 and 102. In this configuration in which infant 14 is closely coupled to first sensor 12, it is sufficiently sensitive to detect most movements of infant 14, including respiration movements.

To achieve a uniform sensitivity of first sensor 12 over substantially all the surface of cover 32, first sensor 12 is either implemented as an array of resonant sensors 50 electrically connected in parallel or in series, or as an array of resonant sensors 50 each having its own support circuitry with the outputs thereof summed together. For example, oscillator 42 can drive multiple high impedances 44 each coupled to a resonant sensor 50 in the array. Likewise, multiple integrated buffer amplifiers 54 can be coupled through cables to a multiplexer that samples the buffered sensor signals and conveys them to one or several sensor subsystems 40 for processing.

The overall operation of monitoring system 10 is described below with reference to FIGS. 1, 2, and 8.

Preferred functions of sensor subsystem 40 and controller 26 include:

filtering out noise and electromagnetic interference signal components to extract useful sensor signals from the various sensor signals;

separating from the useful sensor signals a respiration-related signal and a nonrespiration-related signal;

differentiating or eliminating from the useful sensor signal, other signals that are caused by vibrations and movements of other objects, animals, or persons in the proximity sensor subsystem 40;

interpreting the various signals received from the sensors including audio, accelerometric, humidity, movement, proximity, ECG, oxygen saturation, sleeping position, and temperature signals;

analyzing the respiration-related signal and the nonrespiration-related signal;

inhibiting alarms if certain sensor signals are present and are in a predetermined range, or if the overall multidimensional signal, determined with the whole set of sensors acting in conjunction, classifies as a normal pattern;

generating warnings or various types of specific alarms if certain sensor signals are absent or present and in a predetermined range, or if the overall multidimensional signal determined with the whole set of sensors acting in conjunction classifies as an abnormal pattern;

optionally generating warnings if infant 14 is moving according to an abnormal pattern of movement indicative of agitation; and optionally remotely communicating with communications unit 28.

In particular, when infant 14 is moving in the bed, first sensor 12 detects the movement, and the resulting first sensor signal is processed through buffer amplifier 54, detector 56, filter 58, and amplifier 60 to produce a conditioned first sensor signal. Filter 58 mainly removes power supply noise frequencies from 50/60 Hz to about 100/120 Hz and higher noise frequencies ranging from about 150 Hz to about 200 Hz.

Figure 8:
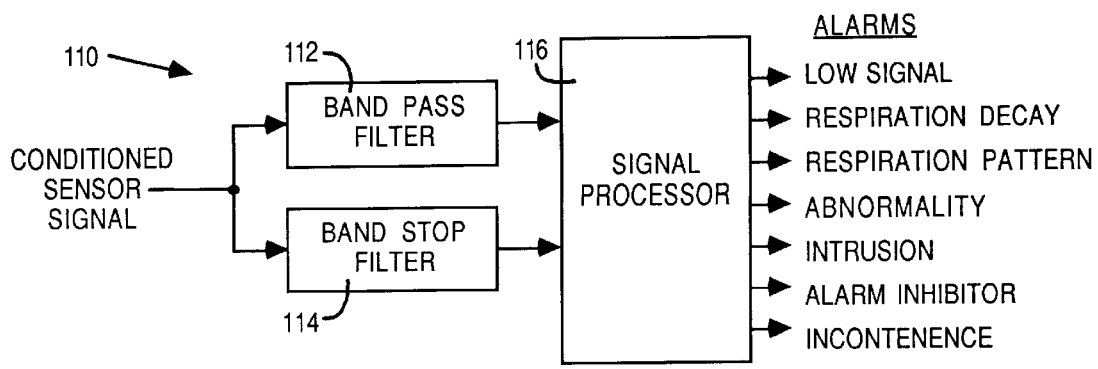
FIG. 8 is a simplified electrical block diagram of a signal filtering subsystem of this invention.

Referring to FIG. 8, the conditioned first sensor signal is preferably further processed by a filtering and processing block 110 that receives the conditioned first sensor signal from amplifier 60 or from a digital representation thereof generated by ADC 64. Filtering and processing block 110 includes at least one of analog and digital filters and/or processes to separate and isolate from first sensor signal a respiration-related signal and a nonrespiration-related signal. The processing preferably employs a band-pass filter 112 to extract the respiration-related signal, and a band-stop filter 114 to extract the nonrespiration-related signal. Filters 112 and 114 are preferably tunable to account for the age-related average respiration rate of infant 14.

In one embodiment the extracted signals are conveyed to a signal processor 116 that performs a signal level decision process, which compares the signal values of the two extracted signals with predetermined thresholds, and if neither of the extracted signals exceeds its predetermined threshold for a predetermined time period, such as two to five seconds, a low signal alarm is generated.

In one embodiment signal processor 116 optionally generates from the respiration-related signal a self-correlation signal and determines the decay period of the correlation signal. If the decay period is less than a predetermined threshold value, a respiration decay alarm signal is generated.

Signal processor 116 optionally performs a pattern matching operation in which a period of the respiration-related signals is processed to store a respiration-related period pattern in a memory. Signal processor 116 compares a subsequently received respiration-related signal period to the previously stored period pattern. If a pattern matching does not occur, a respiration pattern alarm is generated. This alarm may also be caused by agitation of infant 14.

If monitoring system 10 includes at least one optional second sensor 18, a second sensor signal is generated and conditioned as for the first signal to generate a conditioned second sensor signal that is compared with the respiration- and nonrespiration-related signals extracted from first sensor 12. If the second sensor signal does not exceed a predetermined threshold, then infant 14 is laying down (not-proximal to second sensor 18), and the second sensor signal is uncorrelated with the respiratory-related signal extracted from first sensor 12. If the second sensor signal exceeds the predetermined threshold, an abnormality alarm is generated indicative of an abnormal situation, such as high vibrations of support platform 16, agitation of infant 14, or a system malfunction. If the second sensor signal does not exceed the predetermined threshold and is not correlated with the movement-related signal extracted from the first sensor signal, then the situation is interpreted as external proximal object 20 approaching second sensor 18, and a safety perimeter intrusion alarm is generated.

If monitoring system 10 includes at least one optional accelerometric sensor 22, an accelerometer signal is generated that is compared to the first sensor signal to increase the reliability of detection in a manner similar to that described for second sensor 18. Moreover, first sensor 12 and accelerometric sensor 22 can detect small movements caused by heart beats in infant 14, thereby adding a redundancy signal for further interpreting the status of infant 14.

If monitoring system 10 includes optional audio detector unit 24, an audio signal is generated in response to sounds associated with infant 14, external proximal object 20, or other environmental sources. If the audio signal level exceeds a predetermined threshold, signal processor 116 interprets the situation as a vocal sound from infant 14, and generates an alarm inhibitor signal.

If monitoring system 10 includes humidity sensor 104, a humidity signal is generated in response to detected moisture. If the humidity signal level exceeds a predetermined threshold, signal processor 116 interprets the situation as an incontenence state of infant 14, and generates an incontenence alarm.

If monitoring system 10 includes optional sensors for determining the ambient temperature or the position, blood oxygen saturation level, or ECG activity of infant 14, the relevant sensor signals are processed and analyzed in conjunction with the previously described signals to determine the risk factors and state of infant 14 and to generate appropriate warnings or alarms.

Referring again to FIG. 1, monitoring system 10 may further include a miniature, low-power RF generator 120 that is preferably attached to the back of the clothing worn by infant 14. RF generator 120 preferably provides a less than about 1 microwatt, 10 MHz to 100 MHz RF signal that pulses on about once every 10 seconds for a duration of about 1 millisecond or less. The frequency of RF generator 120 is chosen to be well separated from the frequency of oscillator 42, but is still readily detectable by first sensor 12. The RF signal is received by first sensor 12, which acts as an antenna, and couples the received RF signal through a high impedance input circuit to controller 26.

When infant 14 is positioned on his or her back as shown in FIG. 1, RF generator 120 is closely spaced apart from first sensor 12 and the RF signal received by first sensor 12 is maximized and, consequently, exceeds a maximal threshold value that is set in accordance with the overall amplification of first sensor 12 and controller 26. On the other hand, when infant 14 is positioned facing support platform 16, RF generator 120 is spaced farther apart from first sensor 12 and, accordingly, the RF signal strength received by first sensor 12 is reduced to less than a medial threshold value that is less than the maximal threshold value. When the RF signal is less than the medial threshold value, a warning signal is generated indicating that infant 14 is in an improper sleeping position. Finally, if infant 14 stands on support platform 16 or leaves the vicinity of first sensor 12, the RF signal strength is further reduced to less than a minimal threshold value and an appropriate warning signal may be generated.

In another embodiment, RF generator 120 generates more frequent pulses, e.g., 10 pulses per second, and the low-amplitude, low-frequency changes in the received signal strength are detected and filtered to produce a low-frequency signal that represents respiratory and other movements that can be used in cooperation with the signal from first sensor 12 to detect abnormal situations.

RF generator 120 constitutes an "electronic tag" which, in an alternative embodiment, may also include at least one of an ECG sensor, a blood oxygen saturation sensor, and a skin temperature sensor to monitor various states and conditions of infant 14. In this embodiment, certain ones of the sensors or RF generator 120 are placed in contact with the skin of infant 14. The resulting signals are employed to modulate the RF signal using well-known techniques for transmission to first sensor 12 and detection by controller 26.

The classification and decision processes controlling the warning and alarm generation process also include system data inputs for specific personal, family history, and ambient factors that influence the risk of SIDS and, therefore, the classification and decision processes. In particular, system data inputs may include some combination of:

i) the age of infant 14;
ii) family history (e.g., previous infant death of siblings);
iii) maternal history (e.g. mother smoking before infant is born);
iv) smokers in the infant 14 environment;
v) ambient temperature;
vi) health state of infant 14, mainly respiratory and cardiovascular (as determined by physicians during data input); and
viii) sleeping position.

According to these factors, the thresholds and/or the global pattern classification and decision processes are adjusted.

Skilled workers will understand that, by modifying the dimensions of the resonant sensor and the parameters of the signal processor, the invention can be adapted to monitoring adult subjects.

Based on the RF signal, alarm, and alarm inhibitor signals described above, signal processor 116 makes aggregated decisions to generate specific warnings when a critical situation occurs, such as when no respiration-related signal is detected during a predetermined time period, when an intruder enters the safety perimeter surrounding monitoring system 10, or when an abnormality is detected.

Optional remote control unit 30 transmits control information and receives alarms from communications unit 28 that may be conveyed employing various techniques, such as radio frequencies, infrared, ultrasound, and conventional cabling. Remote control unit generates appropriate remote warning signals, optionally reproduces the audio signal, and may optionally include circuitry supporting two-way audio communication.

Skilled workers will understand how to implement and program monitoring system 10 to perform the above-described functions. In particular, some combination of binary logic, fuzzy logic, and neural networks may be employed to improve the quality of the overall classification, decision, and warning/alarm system.

Monitoring system 10 is advantageous because it:

requires no physical attachments to the monitored subject or infant 14;

is safe and effective for monitoring human infants;

has a low false alarm rate;

can be implement in a compact form factor;

has sensing configurations and sensing areas that are readily adaptable to various subject monitoring applications;

is readily adapted to sense and interpret incontinence, sounds, and movements generated by infant 14 and its environment; and it is able to detect the objects entering or infant 14 escaping from the safety perimeter.

Physical attachments include any sensor, sensor wire, bellows, microphone, or sensor tube, that is strapped, taped, glued, electrically or pneumatically connected, or otherwise physically attached to infant 14.

Beyond generating warnings and alarms, monitoring system 10 may be provided with active devices, such as to produce sounds and movements of support platform 16 to awaken or revive infant 14 and to start artificial ventilation of infant 14 under appropriately detected conditions.

It will be obvious to those having skill in the art that many changes may be made to the details of the above-described embodiments of this invention without departing from the underlying principles thereof. The scope of the present invention should, therefore, be determined only by the following claims.

We claim:

1. An apparatus for monitoring respiration and movements of an infant positioned adjacent to a supporting platform, comprising:

a first sensor positioned between the infant and the support platform, the first sensor not having a physical attachment to the infant and including a distributed inductance and distributed capacitance device formed as a radially wound spiral flat conductor strip that produces a uniform electric field for sensing the respiration and movements of the infant the first sensor further having an impedance that is a function of a frequency, the impedance having a maximum value when the frequency equals a resonant frequency of the first sensor, the resonant frequency varying as a function of the respiration and movements of the infant;

an oscillator generating a signal having an operating frequency that substantially equals or is close to the resonant frequency of the first sensor;

a high-impedance element coupling the signal from the oscillator to the first sensor, the high-impedance element and the first sensor forming a voltage divider that produces from the signal a sensor voltage that is proportional to the impedance of the first sensor and is, therefore, responsive to the respiration and movements of the infant;

a detector extracting from the sensor voltage a first signal representative of the respiration and movements of the infant;

a controller receiving the first signal and including a band-pass filtering function to extract from the first signal a respiration-related signal and a band-stop filtering function to extract from the first signal a movement-related signal; and a signal processor processing at least one of the respiration-related signal and the movement-related signal to generate an alarm signal.

2. The apparatus of claim 1 in which the band-pass filter function has a tunable bandwidth and the band-stop filter function has a tunable cutoff frequency, the tunable bandwidth and cutoff frequency being adjustable to account for an age-related average respiration rate of the infant.

3. The apparatus of claim 1 in which the support platform includes at least one of a crib and an incubator.

4. The apparatus of claim 1 in which the first sensor is enclosed in at least one of a comforter, a quilt, a sheet, a bedspread, a pane, a counterpane, and a fancy.

5. The apparatus of claim 1 in which the resonant circuit is formed on a major surface of a thin flexible plastic substrate.

6. The apparatus of claim 1 in which the resonant circuit is formed from a material including at least one of a thin metallic film, a thick conductive film, and a conductive polymeric film.

7. The apparatus of claim 1 in which the resonant circuit includes first and second major surfaces, and a sponge sheet is positioned adjacent to at least one of the first and second major surfaces.

8. The apparatus of claim 1 in which the first sensor includes an array of resonant circuits each formed as a spiral conductor, and in which the array of resonant circuits are electrically connected in at least one of a parallel circuit or a series circuit.

9. The apparatus of claim 1 in which the first sensor includes an array of resonant circuits each formed as a spiral conductor, and in which each resonant circuit in the array has an associated generator and an associated output signal, the output signals being summed combined to form the first signal.

10. The apparatus of claim 1 further including at least one second sensor that is spaced apart from the first sensor, the second sensor defining a safety perimeter around the infant, and in which the controller receives from the second sensor a second signal indicative of at least one of a proximity to the safety perimeter of the infant and a proximity to the safety perimeter of an external object.

11. The apparatus of claim 1 further including at least one accelerometric sensor that generates an acceleration signal indicative of movements of the support platform, the signal processor comparing the acceleration signal and the first sensor signal to increase a reliability of detecting movements of the infant.

12. The apparatus of claim 1 further including an audio detector that generates an audio signal indicative of sounds associated with the infant, the signal processor inhibiting the alarm signal if the audio signal exceeds a predetermined threshold level.

13. The apparatus of claim 1 further including a remote control unit for two-way communicating with the controller control information, and at least one of the alarm signal and an audio signal.

14. The apparatus of claim 13 in which the communicating employs at least one of a radio frequency link, an infrared link, an ultrasound link, and an electrical cable.

15. The apparatus of claim 1 further including a radio frequency generator mechanically coupled to the infant, the radio frequency generator producing a radio frequency signal that is received by the first sensor and having multiple signal strengths that are dependent on a varying distance between the generator and the first sensor and are, therefore indicative of multiple body positions of the infant, at least one of the signal strengths being interpreted by the controller as a prone body position.

16. The apparatus of claim 15 further including at least one of an electrocardiogram ("ECG") sensor and a blood oxygen saturation sensor coupled to the infant for generating at least one of an ECG signal and a blood oxygen saturation signal that modulates the radio frequency generator such that the radio frequency signal includes modulation that is interpreted by the controller as at least one of an ECG pattern and a blood oxygen saturation level of the infant.

17. The apparatus of claim 16 further including a temperature sensor that provides a temperature signal indicative of an ambient temperature in the vicinity of the infant, the controller receiving the radio frequency signal, the ECG signal, the blood oxygen saturation signal, and the temperature signal and determining on the basis of an overall signal pattern whether to generate a warning signal.

18. A method for monitoring respiration and movements of an infant positioned adjacent to a supporting platform, the method comprising:

positioning a first sensor between the infant and the support platform, the first sensor not physically attached to the infant and including a distributed inductance and distributed capacitance device formed as a radially wound spiral flat conductor strip that produces a uniform electric field for sensing the respiration and movements of the infant, the first sensor further having an impedance that is a function of a frequency, the impedance having a maximum value when the frequency equals a resonant frequency of the first sensor, the resonant frequency varying as a function of the respiration and movements of the infant;

generating a signal having an operating frequency that substantially equals or is close to the resonant frequency of the first sensor;

coupling the signal to the first sensor with a high-impedance element, the high-impedance element and the first sensor forming a voltage divider that produces from the signal a sensor voltage that is proportional to the impedance of the first sensor and is, therefore, responsive to the respiration and movements of the infant;

detecting the sensor voltage to produce a first signal representative of the respiration and movements of the infant;

band-pass filtering the first signal to extract a respiration-related signal;

band-stop filtering the first signal to extract a movement-related signal; and processing at least one of the respiration-related signal and the movement-related signal to generate an alarm signal.

19. The method of claim 18 further including positioning at least one second sensor spaced apart from the first sensor for sensing a safety perimeter around the infant, the second sensor generating a second signal indicative of movements proximal to the safety perimeter of at least one of the infant and an external object.

20. The method of claim 19 in which the processing includes interpreting that the infant is laying down adjacent to the first sensor if the second signal does not exceed a predetermined threshold level.

21. The method of claim 26 in which the processing includes generating a safety perimeter intrusion alarm if the second signal does not exceed a predetermined threshold and the second signal is not substantially correlated with the movement-related signal extracted from the first signal.

22. The method of claim 19 in which the processing includes generating an abnormality alarm if the second signal is substantially correlated with the movement-related signal extracted from the first signal, the abnormality alarm being indicative of at least one of a vibration of the supporting platform, an agitated movement of the infant, and a malfunction.

23. The method of claim 18 further including mechanically coupling a radio frequency generator to the infant, the radio frequency generator producing a radio frequency signal that is received by the first sensor at multiple signal strengths that are dependent on a varying distance between the generator and the first sensor and are, therefore, indicative of multiple body positions of the infant and interpreting at least one of the signal strengths as a prone body position.

24. The method of claim 23 further including generating a monitoring signal indicative of at least one of an electrocardiogram ("ECG") pattern and a blood oxygen saturation level of the infant, modulating the radio frequency signal with the monitoring signal, and detecting from the modulated radio frequency signal at least one of the ECG pattern and the blood oxygen saturation level of the infant.

25. The method of claim 24 further including generating a temperature signal indicative of an ambient temperature in the vicinity of the infant, and determining whether to generate a warning signal by analyzing an overall signal pattern established by the modulated radio frequency signal, the monitoring signal, and the temperature signal.

26. The method of claim 25 further including awakening the infant with at least one of a loud sound and a movement in response to at least one of the alarm signal and the warning signal.

27. The method of claim 25 further including ventilating the infant with an artificial respirator in response to at least one of the alarm signal and the warning signal.

28. The method of claim 23 further including producing a signal strength pattern from the multiple signal strengths, and extracting a secondary respiration signal from the signal strength pattern.

29. The method of claim 18 in which the processing further includes classifying and deciding processes that are based on a medical and family history of the infant, the medical and family history including at least one of an age, a sex, a birthweight, a drug therapy history, a respiratory state, and an infectious state of the infant, and at least one of an age and a smoking status of a mother of the infant.

30. The method of claim 29 in which the classifying and deciding processes employ at least one of a binary logic process, a fuzzy logic process, and a neural network process.

31. The method of claim 18 in which the processing further includes:

determining from the respiration-related signal sets of respiration rates and associated respiration waveform patterns;

storing the sets of respiration rates and associated respiration waveform patterns in a memory;

comparing a subsequently received respiration rate and an associated respiration waveform pattern to at least one of the previously stored sets of respiration rates and associated respiration waveform patterns, and generating a respiration rate pattern alarm if the subsequently received respiration rate pattern does not substantially match at least one of the previously stored respiration rate patterns.

* * * * *